United States Patent [19]
Kanauchi et al.

[11] Patent Number: 5,453,282
[45] Date of Patent: Sep. 26, 1995

[54] DIETARY LIPID DIGESTION-ABSORPTION INHIBITORY AGENTS AND INGESTA

[75] Inventors: Osamu Kanauchi; Keiji Deuchi, both of Shibuya, Japan

[73] Assignee: Kirin Beer Kabushiki Kaisha, Tokyo, Japan

[21] Appl. No.: 35,677

[22] Filed: Mar. 23, 1993

[30] Foreign Application Priority Data

Mar. 24, 1992 [JP] Japan ................................ 4-066242
Mar. 22, 1993 [JP] Japan ................................ 5-062112

[51] Int. Cl.$^6$ ............................................ A61K 9/20
[52] U.S. Cl. ...................... 424/464; 424/489; 424/451; 424/458
[58] Field of Search ................... 424/451, 464, 424/485, 468, 489

[56] References Cited

U.S. PATENT DOCUMENTS 4,738,850  4/1988  Thakur et al. ........................ 424/464
4,963,367  10/1990  Ecanow ................................ 424/485

FOREIGN PATENT DOCUMENTS 1-211529  8/1989  Japan.
1-258623  10/1989  Japan.

OTHER PUBLICATIONS

English Abstract of JP1211529, WPI Accession No. 89–288840/40.
English Abstract of JP1258623, WPI Accession No. 89–345129/47.

*Primary Examiner*—Thurman K. Page
*Assistant Examiner*—William E. Benston, Jr.
*Attorney, Agent, or Firm*—Ladas & Parry

[57] ABSTRACT

Disclosed herein are dietary lipid digestion-absorption inhibitory agents and ingesta, comprising as an active ingredient a mixture of chitosan and ascorbic acid or a salt thereof. Also disclosed is a therapeutic method for obesity, which comprises administering an effective amount of a mixture of chitosan and ascorbic acid or salt thereof to a person who requires treatment for obesity.

8 Claims, No Drawings

5,453,282

DIETARY LIPID DIGESTION-ABSORPTION INHIBITORY AGENTS AND INGESTA

BACKGROUND OF THE INVENTION

Field of the Art

The present invention relates to dietary lipid digestion-absorption inhibitory agents and ingesta which are expected to have a dietary lipid absorption inhibitory effect, an obesity preventing effect and the like.

Related Art

In recent years, intake of lipid is increasing with the improvement or westernizing of the eating habits in Japan. According to the report of the "National Nutrition Survey" conducted (in Japan) in the year of 1989, the ratio of caloric intake from lipid is in excess of 25% on an average, and this ratio is already in a danger zone. Such a constant excessive ingestion of lipid causes the problem of obesity, and a variety of its complications, for instance, heart or circulatory diseases, respiratory diseases, diabetes and the like, are becoming even an object of public concern in developed countries.

For this reason, the approaches aiming at removal of body fat or lowering of dietary lipid are now being actively made in many countries, and a variety of methods, medicines and commodities as described below have been proposed.

First of all, the intake of lipid can be restricted by alimentotherapy, fat substitutes, or anorectic agents. Alimentotherapy is, however, attended with great difficulties when it is practiced for a prolonged period of time, because this therapy often adopts an excessively restricted diet, whereas lipid-rich tasty foods are abundant in our present-day life. With respect to fat substitutes, a great variety of commodities such as substitutes having a carbohydrate base, a protein base or an oils and fats base, and synthetic fat substitutes have been developed. However, it is not easy with such substitutes to satisfy present-day people, who tend to pursue natural taste and genuine relish. On the other hand, there is a method in which only a feeling of plenitude is obtained by taking konjak mannan or the like, thereby diminishing appetite itself. Such a method is however accepted only by a very few obesity patients because konjak mannan cannot be readily ingested due to their physical properties. Further, mazindol, fenfluramine and the like have been known as anorectic agents. However, these medicines can be administered only under the control of a medical doctor, and their side effects have also been reported [Hadler A. J.: J. Clin. Pharm., 12, 453(1972); and Stunkar D. A., et al: Lanset, 1, 503(1973)].

As a method which can replace the foregoing impracticable methods, there is an approach to prevention of absorbed aliments from being accumulated as fat, without limiting the ingestion of fat and the like. Dehydroepiandrosteron [Yen T. T., et al: Lipid, 12, 409(1977)] can be mentioned as a medicine for this purpose. However, it has been reported that this medicine entails a side effect whereby the hormonal balance is lost [Baulien E. E., et al.: J. Clin. Endocrinal Metal, 23, 1298(1963); and Siiteri P. K., et al.: Steroid, 2, 713(1963)]. Further, it has been known that the hot-taste component (capsicin) of capsicum is useful for promoting the decomposition of accumulated body fat [Kawada T., et al: J. Nutr., 116, 1272(1986)]. However, this component has not yet been put to practical use due to its stimulating taste. The use of thyroid hormone may also be considered because it promotes the decomposition of body lipid. However, it has been pointed out that thyroid hormone is poor in lipid specificity, and that this hormone decreases the amount of muscles rather than that of lipid [Kyle L. H., et al: N. Eng. J. Med., 275, 12(1966); and Gray G. A., et al: Am. J. Clin. Nutr., 26, 715(1973)].

An approach to prevention of ingested lipid from being absorbed by the alimentary canal, which is made to overcome the above-described shortcomings, is attracting public attention these days. However, neomycin, which is known as a medicine having the above effect, gives rise to a serious side effect of causing fatty diarrhea [Falcon W. W., et al: Ann. N. Y. Acad. Sci., 132, 879(1966)]. Capsules of a certain type which can trap dietary lipid at an alimentary canal [Japanese Laid-Open Patent Publication No. 52713/1989], crosslinked products of collagen [Specification of U.S. Pat. No. 4,865,850], and capsule preparations containing sodium polyacrylate as an aggregating agent [Japanese Laid-Open Patent Publication No. 120227/1991] have been disclosed. However, their effects are still unclear, because, for example, we found that the total amount of discharged lipid was not observed in any of the above disclosures. An oral lipid absorber comprising a crosslinked polymer of long-chained alkyl(meth)acrylate has been proposed as a material having a lipid absorption inhibitory effect [Japanese Laid-Open Patent Publication No. 23136/1993].

In recent years, it has been found that chitosan has a lipid absorption inhibitory effect [Nagyvary J. J.: Nutr. Rep. Int., 20, 677(1979); I. Ikeda: J. Nutr., 119, 1383(1989); and Japanese Laid-Open Patent Publication No. 290170/1991], and this effect of chitosan seems to be hopeful. However, in the above studies, the lipid concentration in blood after feeding is adopted as an index, and there are many obscure points in the total balance of lipid. The effects of chitosan of increasing the amount of lipid discharged in the stool and decreasing body lipid, evaluated by using chickens have been reported [Kobayashi, et al: Nihon Kakin Kaishi, 28, 88(1991)]. However, it does not discuss multiplier effects of chitosan and other components.

As described above, various approaches have been made in order to decrease dietary lipid or to reduce body fat, and a variety of materials, commodities and methods have been proposed for this purpose. However, they are not excellent in taste or are harmful to health, so that most of them are abandoned before the purpose is fully attained.

DISCLOSURE OF THE INVENTION

Summary of the Invention

In the light of the aforementioned prior art, an object of the present invention is to provide safe and easily ingestive dietary lipid digestion-absorption inhibitory agents which do not require a diet and can cause a discharge of excessively ingested energy outside the body by inhibiting digestion and absorption of lipid.

In order to attain the above object, the present inventors have carried out extensive researches on materials which have an effect of causing an efficient discharge of ingested dietary lipid outside the body, for example, via the stool. As a result, it was firstly found that a mixture of chitosan and ascorbic acid or its salt has a dietary lipid digestion-absorption inhibiting ability, namely, an ability to cause discharge of dietary lipid into the stool, which is specific to lipid and extremely high as compared with that of only chitosan. The present invention has been accomplished on the basis of the above finding.

That is to say, the dietary lipid digestion-absorption inhibitory agents according to the present invention comprise as an active ingredient a mixture of chitosan and ascorbic acid or a salt thereof.

Further, the dietary lipid digestion-absorption inhibitory ingesta according to the present invention comprise as an active ingredient a mixture of chitosan and ascorbic acid or a salt thereof.

The present invention also relates to a therapeutic method for obesity, which comprises administering an effective amount of a mixture of chitosan and ascorbic acid or a salt thereof to a person who requires treatment for obesity.

Meritorious Effects of the Invention

The above-described mixture of chitosan and ascorbic acid or a salt thereof can be readily ingested, and can cause an efficient discharge of dietary lipid outside the body. Therefore, ingested lipid, that is, energy can be decreased without feeding a restricted diet. The above-described chitosan, ascorbic acid, and salts thereof have been actually used as food additives in Japan, are highly safe, can be used continuously, and can effectively prevent over-ingestion of dietary lipid when they are used or administered continuously. The fact that the above-described mixture of chitosan and ascorbic acid or a salt thereof is extremely effective, in particular, for causing discharge of dietary lipid was firstly and unexpectedly found by us.

Further, by the use of the above mixture, the intake and the number of ingestion times can be considerably decreased as compared with the case where chitosan is singly used. The use of this mixture is therefore extremely effective because of its ease of ingestion and from the economical point of view.

DETAILED DESCRIPTION OF THE INVENTION

The present invention relates to a specific use of chitosan and ascorbic acid or salts thereof.

Chitosan and Ascorbic Acid or Salts Thereof

The chitosan itself for use in the present invention is a known compound, and is described in detail, for example, in "The Last Biomass, Chitin and Chitosan" published in 1988 by Chitin & Chitosan Kenkyukai. In the present invention, it is possible to use chitosan selected from those commercially available.

L-Ascorbic acid or isoascorbic acid can be used as the ascorbic acid in the present invention. Namely, the term "ascorbic acid" used in the present invention is intended to include its isomers. Typical salts of the ascorbic acid are sodium L-ascorbate and sodium isoascorbate, but calcium salts and the like can also be mentioned. These are also known compounds, and L-ascorbic acid, isoascorbic acid and salts thereof are commercially available. It is therefore enough to use ascorbic acid or a salt thereof suitably selected from those commercially available.

The mixing ratio by weight of the chitosan and the ascorbic acid is approximately from 20:1 to 1:2, preferably from 10:1 to 2:1. In the case where the amount of the ascorbic acid is less than that in that in the above ratio, the synergistic effect brought about by the combination use of chitosan and ascorbic acid cannot be expected. On the other hand, when the amount of the ascorbic acid is more than that in the above ratio, the relative intake or dose of the chitosan is decreased, so that only a little dietary lipid digestion-absorption inhibitory effect can be obtained. The above mixing ratio can also be applied to the case where chitosan and a salt of ascorbic acid are used in combination.

A water-soluble salt such as a sodium salt is preferable as the salt of ascorbic acid.

Lipid Digestion-Absorption Inhibitory Agents

The dietary lipid digestion-absorption inhibitory agents of the present invention comprise as an active ingredient a mixture of chitosan and ascorbic acid or a salt thereof.

The dietary lipid digestion-absorption inhibitory agents according to the present invention can be embodied as preparations of themselves, or as capsule or compressed tablet preparations. Further, they can also be embodied in the form of being contained in foods, that is, in the form of dietary lipid digestion-absorption inhibitory ingesta. Since obesity is caused by digestion and absorption of lipid and other aliments, the dietary lipid digestion-absorption inhibitory agents according to the present invention can also be considered as therapeutic agents for obesity, serving as obesity preventing agents or obesity prophylactic agents. The term "therapeutic agents for obesity (obesity preventing or prophylactic agents)" is herein intended to include both obesity prophylactic agents which are used for protecting non-obese people from obesity, and obesity preventing agents which are used for preventing obesity patients from becoming even more obese.

In the present invention, the dietary lipid includes simple lipid represented by triglyceride, phospholipid represented by phosphatidic acid, and glycolipid represented by cerebroside.

Although, the lipid digestion-absorption inhibitory agent is composed of a combination of chitosan and ascorbic acid or a salt thereof, it may further contain auxiliary components as long as they do not mar the function of the agent as an inhibitory agent.

In the present invention, any substance which is harmless for the human body can be used as the auxiliary component which may be incorporated into the inhibitory agent when necessary. Further, the inhibitory agent of the present invention can be made into any form; for instance, it can be made into capsule preparations using a gelatin capsule or the like, tablets, or granules. It is needless to say that it can also be incorporated into ordinary ingesta.

The dose of the inhibitory agent in the case of oral administration is usually from 1 g to 50 g/60 kg body weight per day when expressed by the total amount of the chitosan and the ascorbic acid or a salt thereof. The chitosan, the ascorbic acid and salts thereof are substantially harmless when they are administered orally.

Lipid Digestion-Absorption Inhibitory Ingesta

The lipid digestion-absorption inhibitory ingesta according to the present invention comprise as an active ingredient a mixture of chitosan and ascorbic acid or a salt thereof.

The dietary lipid digestion-absorption inhibitory ingesta can be obtained by incorporating chitosan and ascorbic acid or a salt thereof into ingesta by taking their form into consideration; for example, powdered ones are incorporated into biscuit-like food, and liquefied ones are incorporated into drink-like food. The minimum concentration in feed at which the chitosan and the ascorbic acid or a salt thereof reveal their respective effects was found to be 1% by weight or more when expressed by the amount of chitosan. However, in the present invention, it is desirable that the incorporation amount of the chitosan and the ascorbic acid or a salt thereof be in the range of 2% to 10% by weight of an ingestus.

EXAMPLES

I. Lipid Digestion-Absorption Inhibition

Test Method

SD Male rats (5 weeks old, approximately 150 g) were used in the experiment. They were preliminarily fed with solid feed for one week for acclimatization, and divided into groups, each including 10 rats. The formulation of the feed was as shown in Table 1.

Each mixture was mixed with the feed, and the resultant was given to the rats ad libitum. After one-month breeding, the stools of the rats were collected for three days. The weight of each dried stool was measured, and the lipid content of the stool was determined in accordance with the method by Saxon (Saxon, G. L.: J. Biol. Chem., 17, 99(1914)).

The lipid digestion-absorption rate was calculated by the following equation:

(lipid digestion-absorption rate (%)) ={(the amount of lipid ingested)−(the amount of lipid discharged)}÷(the amount of lipid ingested) ×100

Further, on the last day, the rats were deprived of the feed for one night, and then subjected to autopsy and a blood biochemical test.

At this time, fat tissue of the epididymis was also extracted as an index of visceral depot fat, and weighed.

Example 1

Test Examples 1 to 4 as shown in Table 1 were carried out. The results were as shown in Tables 3 and 4 below.

TABLE 1

Formulation A of Test Feed

| Test Example | |
|---|---|
| 1: | Cellulose powder was administered |
| 2: | Cellulose powder and L-ascorbic acid were administered |
| 3 | Chitosan powder was administered |
| 4: | Chitosan powder and L-ascorbic acid were administered |

| Test Example | 1 | 2 | 3 | 4 |
|---|---|---|---|---|
| Casein | 20.0 | 20.0 | 20.0 | 20.0 (wt %) |
| Sucrose | 48.3 | 46.8 | 48.3 | 46.8 |
| Corn oil | 20.0 | 20.0 | 20.0 | 20.0 |
| Choline chloride | 0.2 | 0.2 | 0.2 | 0.2 |
| Vitamin mixture | 1.0 | 1.0 | 1.0 | 1.0 |
| Mineral mixture | 3.5 | 3.5 | 3.5 | 3.5 |
| Cellulose powder | 7.0 | 7.0 | — | — |
| Chitosan powder | — | — | 7.0 | 7.0 |
| L-Ascorbic acid | — | 1.5 | — | 1.5 |

*Vitamin mixture and mineral mixture were prepared in accordance with the prescription of AIN-76.
*Chitosan powder manufactured by Katakura Chikkarin Co., Ltd. was used.

Example 2

The effect of the agents of the present invention on the dietary lipid digestion-absorption rate was observed in accordance with Example 1, by changing the mixing ratio of the chitosan and the ascorbic acid or a salt thereof, and the administration amount thereof. The dietary lipid digestion-absorption rates, which were obtained by giving the feeds having the formulations shown in Table 2, wherein the mixing ratio of chitosan and L-ascorbic acid was 2:3, 10:3 or 10:1, and the administration amount of the mixture thereof was 2.5 wt %, 6.5 wt % or 11.0 wt % of the feed, are shown in Table 5 as examples. Further, the dietary lipid digestion-absorption rate at the time when the mixing ratio of chitosan and isoascorbic acid or a salt of ascorbic acid was made to 10:3, and the administration amount thereof was made to 6.5 wt % of the feed, is also shown in Table 5. It is to be noted that a group to which ascorbic acid or a salt thereof is not given was provided as a control in each case.

TABLE 2

Formulation B of Test Feed

| Test Example | |
|---|---|
| 5: | Product 1 of the Invention: the mixing ratio of chitosan and L-ascorbic acid = 2:3; the product content in the feed = 2.5%. |
| 6: | Control group 1: the L-ascorbic acid is eliminated from the product in Test Example 5. |
| 7-a: | Product 2-a of the Invention: the mixing ratio of chitosan and L-ascorbic acid = 10:3; the product content in the feed = 6.5%. |
| 7-b: | Product 2-b of the Invention: the mixing ratio of chitosan and sodium L-ascorbate = 10:3; the product content in the feed = 6.5%. |
| 7-c: | Product 2-c of the Invention: the mixing ratio of chitosan and isoascorbic acid = 10:3; the product content in the feed = 6.5%. |
| 7-d: | Product 2-d of the Invention: the mixing ratio of chitosan and sodium isoascorbate = 10:3; the product content of the feed = 6.5%. |
| 8: | Control group 2: the L-ascorbic acid is eliminated from the product in Test Example 7-a. |
| 9: | Product 3 of the Invention: the mixing ratio of chitosan and L-ascorbic acid = 10:1; the product content in the feed = 11.0%. |
| 10: | Control group 3: the L-ascorbic acid is eliminated from the product in Test Example 9. |

| Test Example | 5 | 6 | 7(a–d) | 8 | 9 | 10 |
|---|---|---|---|---|---|---|
| Casein | 20.0 | 20.0 | 20.0 | 20.0 | 20.0 | 20.0 |
| Sucrose | 52.8 | 54.3 | 48.8 | 50.3 | 44.3 | 45.3 |
| Corn oil | 20.0 | 20.0 | 20.0 | 20.0 | 20.0 | 20.0 |
| Choline chloride | 0.2 | 0.2 | 0.2 | 0.2 | 0.2 | 0.2 |
| Vitamin mixture | 1.0 | 1.0 | 1.0 | 1.0 | 1.0 | 1.0 |
| Mineral mixture | 3.5 | 3.5 | 3.5 | 3.5 | 3.5 | 3.5 |
| Product 1 of the Invention | 2.5 | — | — | — | — | — |
| Products 2a–d of the Invention | — | — | 6.5 | — | — | — |
| Product 3 of the Invention | — | — | — | — | 11.0 | — |
| Product 4 of the Invention | — | — | — | — | — | — |
| Chitosan | — | 1.0 | — | 5.0 | — | 10.0 |

*Vitamin mixture and mineral mixture were prepared in accordance with the prescription of AIN-76.
*Chitosan powder manufactured by Kimitsu Chemical Co., Ltd. was used.

Results

The results of the above test examples are as shown in Tables 3, 4 and 5.

As shown in Tables 3 and 4, the lipid digestion-absorption rate is lowered by the co-administration of chitosan and ascorbic acid or a salt thereof more significantly than by the single administration of ascorbic acid or chitosan. On the other hand, this synergistic effect was not observed when chitosan was used together with other organic acids. It was found in all of the groups that the protein digestion-absorption rate was scarcely affected by the co-administration of chitosan and ascorbic acid or a salt thereof. Further, the weight of fat tissue of the epididymis per body weight, which is an index of visceral depot lipid, was significantly low in the chitosan-ingested groups, and it was further decreased in the groups to which chitosan and ascorbic acid were administered at the same time. Furthermore, as shown in Table 5, the lipid digestion-absorption rate is significantly lowered when approximately 2% of the mixture of the present invention is added to the feed, and it is further lowered when ascorbic acid or a salt thereof is added to chitosan in a certain proportion.

It is noted that no abnormality was found in all of the groups either in a blood biochemical test or in autopsy conducted on the final day of the test period.

TABLE 3

Weight of Dried Stool and Analytical Results of Lipid Contained in Stool

|  | Weight of Dried Stool (g/3 days) | Amount of Lipid Discharged in Stool (mg/g stool) | Lipid Digestion-Absorption Rate (%) |
| --- | --- | --- | --- |
| Test Example 1 | 5.33 ± 0.30 | 120.5 ± 8.2 | 94.8 ± 0.3[a] |
| Test Example 2 | 5.47 ± 0.27 | 117.1 ± 5.1 | 94.4 ± 0.2[a] |
| Test Example 3 | 6.59 ± 0.80 | 341.5 ± 49.9 | 66.6 ± 8.8[b] |
| Test Example 4 | 13.44 ± 1.73 | 506.5 ± 44.2 | 35.9 ± 8.9[c] |

In the table, the numerical values are in MEAN ± S.E.M., and "a", "b" and "c" denote that there is a significant difference ($p < 0.05$) among the groups.

TABLE 4

Weight of Fat Tissue Surrounding Epididymis

|  | Weight of Fat Tissue (g/100 g body weight) |
| --- | --- |
| Test Example 1 | 1.51 ± 0.08[a] |
| Test Example 2 | 1.46 ± 0.16[a] |
| Test Example 3 | 0.71 ± 0.02[b] |
| Test Example 4 | 0.60 ± 0.03[c] |

In the table, the numerical values are in MEAN ± S.E.M., and "a", "b" and "c" denote that there is a significant difference ($p < 0.05$) among the groups.

TABLE 5

Lipid Digestion-Absorption Rate

|  | Lipid Digestion-Absorption Rate (%) |
| --- | --- |
| Test Example 5 | 93.9 ± 0.3* |
| Test Example 6 | 96.4 ± 0.3 |
| Test Example 7a | 64.3 ± 6.3* |
| Test Example 7b | 56.2 ± 7.0* |
| Test Example 7c | 59.0 ± 8.5* |
| Test Example 7d | 62.6 ± 9.5* |
| Test Example 8 | 83.9 ± 3.9 |
| Test Example 9 | 26.9 ± 8.3* |
| Test Example 10 | 48.4 ± 8.4 |

In the table, the numerical values are in MEAN ± S.E.M., and "*" denotes that there is a significant difference ($p > 0.05$) between the group and its control.

Example 3

Three healthy male volunteer subjects were continuously fed with predetermined high-fat diets (breakfast and midday meal: lunch with fried chicken as a main dish, supper: regular meal with a pork cutlet as a main dish). During the test period, 5 g/time of the product of the invention (a 10:1 mixture of chitosan and sodium ascorbate) was administered (twice a day) to the subjects after a meal for two days. Moreover, a cellulose powder was also administered to the same subjects for other two days as a control. In the afternoon on the day after and two days after the administration of the product of the invention, stools were collected from the subjects and subjected to the analysis in accordance with Example 1. The results are shown in Table 6.

It was confirmed that the amount of stool, the lipid content of stool, and the total amount of lipid discharged in stool were considerably increased also when the product of the invention was administered to a human.

TABLE 6

Amount of Stool and Lipid Content of Stool (Total for 2 Days)

|  | Weight of Wet Stool (g/2 days) | Lipid Content of Stool (mg/g stool) | Total Amount of Lipid Discharged in Stool (g/2 days) |
| --- | --- | --- | --- |
| Control Group (Cellulose) | 319 | 28.8 | 8.8 |
| Test group (Product of the Invention) | 512 | 66.9 | 35.8 |

In the table, the numerical values are the mean values.

Example 4

A tablet preparation of chitosan-ascorbic acid mixture having the formulation shown in Table 7 was obtained.

This preparation was found to be excellent in compressibility, abrasiveness and intragastric decomposability.

TABLE 7

Formulation of Tablet

| Ingredient | Weight (%) |
| --- | --- |
| Chitosan | 80 |
| Ascorbic acid | 10 |
| Cornstarch | 10 |
| Total | 100 |

II. Dietary Lipid Digestion-Absorption Inhibitory Ingesta

Example 5

A drink containing 20% of peach juice, having the formulation shown in Table 8 was prepared.

Example 6

A dough having the formulation shown in Table 9 was prepared, made into a desired shape, and baked in an oven at a temperature of 150° C. for 15 minutes, whereby cookies containing a dietary lipid digestion-absorption inhibitory agent of the invention was obtained.

TABLE 8

Formulation of Fruit Juice Containing Dietary Lipid Digestion-Absorption Inhibitory Agent

| Ingredient | Weight (g) |
| --- | --- |
| 100% Peach juice | 210.0 |
| High-quality refined sugar | 100.0 |
| Ascorbic acid | 1.0 |
| Essence | 1.0 |
| Chitosan | 20.0 |

The total volume was adjusted to 1 liter by the addition of water.

TABLE 9

Formulation of Cooky Containing Dietary Lipid Digestion-Absorption Inhibitory Agent

| Ingredient | Weight (g) |
| --- | --- |
| Flour | 120 |
| Cornstarch | 4 |
| Sugar | 60 |
| Condensed milk | 15 |
| Butter | 20 |
| Shortening | 10 |
| Egg | 60 |
| Baking powder | 2 |
| Vanilla | 1 |
| Chitosan | 8 |
| Ascorbic acid | 4 |

What is claimed is:

1. A method for treating obesity in a mammal to be treated, said method comprising administering to the mammal amounts of chitosan and sodium acsorbate effective to treat obesity in said mammal, said chitosan inhibiting digestion and absorption of the lipid into the mammal and said sodium ascotbate enhancing the inhibitory activity of the chitosan.

2. A method for inhibiting digestion-absorption of dietary lipid in the body of a mammal to be treated comprising administering to said mammal chitosan and sodium ascorbate in amounts of effective to reduce the amount of dietary lipid absorbed in the body, said chitosan inhibiting digestion and absorption of the lipid into the body and said sodium ascotbate enhancing the inhibitory activity of the chitosan.

3. A method as claimed in claim 2 wherein said chitosan and sodium ascotbate are administered to the mammal in a mixture wherein the chitosan and sodium ascorbate is present in a weight ratio of from 20:1 to 1:2.

4. A method as claimed in claim 2 wherein said chitosan and sodium ascorbate are administered to the mammal in a tablet wherein the weight ratio of chitosan to sodium ascorbate is from 20:1 to 1:2.

5. A method as claimed in claim 1 wherein the mammal is not obese.

6. A method as claimed in claim 1 wherein the mammal is obese.

7. A method as claimed in claim 1 wherein said chitosan and sodium ascorbate are administered to the mammal in a mixture wherein the chitosan and sodium ascorbate is present in a weight ratio of from 20:1 to 1:2.

8. A method as claimed in claim 1 wherein said chitosan and sodium ascorbate are administered to the mammal in a tablet wherein the chitosan is present with respect to the sodium ascorbate in a weight ratio of from 20:1 to 1:2.

* * * * *